US00PP30269P2

(12) United States Plant Patent
Eveleens

(10) Patent No.: US PP30,269 P2
(45) Date of Patent: Mar. 5, 2019

(54) ***HYDRANGEA* PLANT NAMED 'HORTMABLUSH'**

(50) Latin Name: *Hydrangea macrophylla*
Varietal Denomination: Hortmablush

(71) Applicants: KOLSTER HOLDING B.V., Boskoop (NL); HORTEVE BREEDING B.V., Aalsmeer (NL)

(72) Inventor: Cornelis P. Eveleens, Aalsmeer (NL)

(73) Assignees: Kolster Holding B.V., Boskoop (NL); Horteve Breeding B.V., Alsmeer (NL)

( * ) Notice: Subject to any disclaimer, the term of this patent is extended or adjusted under 35 U.S.C. 154(b) by 0 days.

(21) Appl. No.: 15/731,887

(22) Filed: Aug. 21, 2017

(51) Int. Cl.
*A01H 5/02* (2018.01)

(52) U.S. Cl.
USPC ..... Plt./250
CPC ..... *A01H 5/02* (2013.01)

(58) Field of Classification Search
USPC ..... Plt./250
See application file for complete search history.

*Primary Examiner* — Anne Marie Grunberg
(74) *Attorney, Agent, or Firm* — C. A. Whealy

(57) ABSTRACT

A new and distinct cultivar of *Hydrangea* plant named 'Hortmablush', characterized by its upright to broadly spreading plant habit; moderately vigorous growth habit and moderate growth rate; freely branching habit with strong and thick sturdy stems; strong root system; mophead-type inflorescences with numerous red purple and white bi-colored sterile flowers; and good postproduction longevity.

2 Drawing Sheets

Botanical designation: *Hydrangea macrophylla.*
Cultivar denomination: 'HORTMABLUSH'.

BACKGROUND OF THE INVENTION

The present invention relates to a new and distinct cultivar of *Hydrangea* plant, botanically known as *Hydrangea macrophylla*, commercially referred to as a mophead-type *Hydrangea* and hereinafter referred to by the name 'Hortmablush'.

The new *Hydrangea* plant is a product of a planned breeding program conducted by the Inventor in Boskoop, The Netherlands. The objective of the breeding program was to create new *Hydrangea* plants with strong root system and large inflorescences with numerous bi-colored sterile flowers and good postproduction longevity.

The new *Hydrangea* plant originated from a cross-pollination made by the Inventor in April, 2006 in Boskoop, The Netherlands, of a proprietary selection of *Hydrangea macrophylla* identified as code number 03-015-06, not patented, as the female, or seed, parent with a proprietary selection of *Hydrangea macrophylla* identified as code number 02-029-06, not patented, as the male, or pollen, parent. The new *Hydrangea* plant was discovered and selected by the Inventor as a single flowering plant from within the progeny of the stated cross-pollination in a controlled greenhouse environment in Boskoop, The Netherlands in July, 2014.

Asexual reproduction of the new *Hydrangea* plant by vegetative terminal cuttings in a controlled environment in Boskoop, The Netherlands has shown that the unique features of this new *Hydrangea* plant are stable and reproduced true to type in successive generations.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Hortmablush'. These characteristics in combination distinguish 'Hortmablush' as a new and distinct *Hydrangea* plant:

1. Upright to broadly spreading plant habit.
2. Moderately vigorous growth habit and moderate growth rate.
3. Freely branching habit with strong and thick sturdy stems.
4. Strong root system.
5. Mophead-type inflorescences with numerous red purple and white bi-colored sterile flowers.
6. Good postproduction longevity.

Plants of the new *Hydrangea* can be compared to plants of the female parent selection. Plants of the new *Hydrangea* differ primarily from plants of the female parent selection in sterile flower color as sterile flower sepals of plants of the female parent selection are solid red purple in color.

Plants of the new *Hydrangea* can be compared to plants of the male parent selection. Plants of the new *Hydrangea* differ primarily from plants of the male parent selection in growth habit as plants of the new *Hydrangea* are stronger and have stronger root systems than plants of the male parent selection. In addition, plants of the new *Hydrangea* are more freely branching than plants of the male parent selection.

Plants of the new *Hydrangea* can be compared to plants of the *Hydrangea macrophylla* 'Harlequin', not patented. In side-by-side comparisons plants of the new *Hydrangea* differ primarily from plants of 'Harlequin' in the following characteristics:

1. Plants of the new *Hydrangea* are more compact than and not as tall as plants of 'Harlequin'.
2. Plants of the new *Hydrangea* are more freely branching than plants of 'Harlequin'.

3. Plants of the new *Hydrangea* have stronger lateral branches than plants of 'Harlequin'.
4. Plants of the new *Hydrangea* have sturdier sterile flowers than plants of 'Harlequin'.

Plants of the new *Hydrangea* can also be compared to plants of the *Hydrangea macrophylla* 'Hortmaserena', not patented. In side-by-side comparisons plants of the new *Hydrangea* differ primarily from plants of 'Hortmaserena' in the following characteristics:

1. Plants of the new *Hydrangea* have shorter lateral branches than plants of 'Hortmaserena'.
2. Plants of the new *Hydrangea* and 'Hortmaserena' differ in sterile flower color as plants of 'Hortmaserena' have sterile flower sepals that are darker red purple in color with narrower white-colored margins.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet is a side perspective view of a typical flowering plant of 'Hortmablush'.

The photograph on the second sheet is a close-up view of a typical inflorescence of 'Hortmablush'.

DETAILED BOTANICAL DESCRIPTION

Plants used in the aforementioned photographs and in the following description were grown during the late spring in 17-cm containers in a glass-covered greenhouse in Boskoop, The Netherlands and under cultural practices typical of commercial *Hydrangea* production. During the production of the plants, day temperatures ranged from 18° C. to 25° C. and night temperatures ranged from 16° C. to 17° C. Plants of the new *Hydrangea* were two years old when the photographs and description were taken. Plants of the new *Hydrangea* are not typically treated with aluminum sulfate to "blue" the inflorescences. In the following description, color references are made to The Royal Horticultural Society Colour Chart, 2015 Edition, except where general terms of ordinary dictionary significance are used.

Botanical description: *Hydrangea macrophylla* 'Hortmablush'.

Parentage:

*Female, or seed, parent*.—Proprietary selection of *Hydrangea macrophylla* identified as code number 03-015-06, not patented.

*Male, or pollen, parent*.—Proprietary selection of *Hydrangea macrophylla* identified as code number 02-029-006, not patented.

Propagation:

*Type cutting*.—By vegetative terminal cuttings.

*Time to initiate roots, summer*.—About three weeks at temperatures about 15° C. to 25° C.

*Time to produce a rooted young plant, summer*.—About six weeks at temperatures about 15° C. to 25° C.

*Root description*.—Medium in thickness, fibrous; typically creamy white in color, actual color of the roots is dependent on substrate composition, water quality, fertilizer type and formulation, substrate temperature and physiological age of roots.

*Rooting habit*.—Moderately freely branching; medium density; strong root system.

Plant description:

*Plant and growth habit*.—Upright and broadly spreading plant habit; overall plant shape is flattened globular; strong and sturdy lateral branches; moderate growth rate and moderately vigorous growth habit.

*Plant height*.—About 42 cm.

*Plant diameter or area of spread*.—About 62.3 cm.

Lateral branch description:

*Branching habit*.—Freely branching habit; when pinched, about nine lateral branches develop per plant.

*Length*.—About 20.1 cm.

*Diameter*.—About 7 mm.

*Internode length*.—About 7.5 cm.

*Texture*.—Smooth, glabrous; fully developed, woody.

*Aspect*.—Upright to about 40° from vertical.

*Strength*.—Strong, sturdy.

*Color*.—When developing: Close to 143B. Developed: Close to 144A to 144B; at the internodes, tinged with close to 187A; when woody, close to 199A and 199B.

*Lenticels*.—Density: Sparse. Length: About 2 mm. Diameter: About 0.5 mm. Color: Close to 187A.

Leaf description:

*Arrangement*.—Opposite, simple.

*Length*.—About 13.3 cm.

*Width*.—About 10.3 cm.

*Shape*.—Broadly ovate to elliptic.

*Apex*.—Apiculate.

*Base*.—Obtuse to short attenuate.

*Margin*.—Serrate.

*Texture, upper surface*.—Smooth to very slightly rugose, glabrous.

*Texture, lower surface*.—Smooth to very slightly rugose, surface mostly glabrous, however small tufts of short hairs present at vein axils.

*Venation pattern*.—Pinnate.

*Color*.—Developing leaves, upper surface: Close to 141A. Developing leaves, lower surface: Close to 138A. Fully expanded leaves, upper surface: Darker than between 139A and N189A; venation, close to 144A. Fully expanded leaves, lower surface: Close to 137B; venation, close to 145A to 145B.

*Petioles*.—Length: About 1.4 cm. Diameter: About 3.5 mm by 5 mm. Texture, upper and lower surfaces: Smooth, glabrous. Color, upper and lower surfaces: Close to 144A.

Flower description:

*Flower type and habit*.—Showy sterile flowers and small inconspicuous fertile flowers arranged on mophead-type terminal panicles; panicles globular and slightly flattened in shape; fertile flowers face mostly upright and sterile flowers face upright to outwardly and slightly drooping depending on their position in the inflorescence.

*Fragrance*.—None detected.

*Natural flowering season*.—Plants flower from late spring to late summer in The Netherlands.

*Flower longevity*.—Fertile flowers last about one week on the plant, fertile flowers not persistent; sterile flowers last about six weeks on the plant, sterile flowers persistent.

*Quantity of flowers*.—Freely flowering habit; about 110 fertile flowers per panicle and about 300 sterile flowers per panicle.

*Panicle height*.—About 9.7 cm.

*Panicle diameter*.—About 19.9 cm.

*Fertile flower buds*.—Length: About 4 mm. Diameter: About 3.5 mm. Shape: Obovate. Color: Close to 69D; towards the base, close to 145C to 145D.

*Sterile flower buds*.—Length: About 2 mm. Diameter: About 2.5 mm. Shape: Flattened globular. Color: Close to 68C.

*Fertile flower diameter*.—About 7 mm.

*Fertile flower depth* (*height*).—About 5 mm.

*Sterile flower diameter*.—About 3.9 cm.

*Sterile flower depth* (*height*).—About 1.8 cm.

*Petals, fertile flowers*.—Quantity and arrangement: Four or occasionally five in a single whorl; petals abscise before fully developing. Length: About 3 mm. Width: About 2 mm. Shape: Ovate, concave. Apex: Acute. Base: Cuneate. Margin: Entire. Texture and luster, upper and lower surfaces: Smooth, glabrous; matte. Color, when opening, upper and lower surfaces: Close to 76C; petals abscise before fully developing.

*Petals, sterile flowers*.—Quantity and arrangement: About four in a single whorl. Length: About 3 mm. Width: About 2 mm. Shape: Ovate, concave. Apex: Acute. Base: Cuneate. Margin: Entire. Texture and luster, upper and lower surfaces: Smooth, glabrous; matte. Color: When opening, upper and lower surfaces: Close to 75C to 75D. Fully opened, upper and lower surfaces: Close to 75C to 75D.

*Sepals, fertile flowers*.—Quantity and arrangement: Five or occasionally four in a single whorl. Length: About 2 mm. Width: About 1.5 mm. Shape: Ovate. Apex: Acute. Base: Broadly cuneate. Margin: Entire. Texture and luster, upper and lower surfaces: Smooth, glabrous; matte. Color: When opening, upper and lower surfaces: Close to 150C to 150D slightly tinged with close to 63D. Fully opened, upper and lower surfaces: Close to 150C to 150D slightly tinged with close to 63D; color does not change with development.

*Sepals, sterile flowers*.—Quantity and arrangement: Four or five in a single whorl. Length: About 2.6 cm. Width: About 2.6 cm. Shape: Broadly rhomboidal to broadly ovate. Apex: Bluntly and broadly acute to short apiculate. Base: Cuneate. Margin: Entire to finely irregularly dentate to serrate. Texture and luster, upper and lower surfaces: Smooth, glabrous; matte. Color: When opening, upper surface: Close to 61D; towards the margins, close to NN155A. When opening, lower surface: Close to 62A; towards the margins, close to NN155A. Fully opened, upper surface: Close to 64D; towards the margins, close to NN155A; colors do not change with development. Fully opened, lower surface: Close to between 62A and 63C; towards the margins, close to NN155A; colors do not change with development.

*Pedicels, fertile flowers*.—Length: About 2 mm. Diameter: About 1 mm. Strength: Moderately strong. Aspect: Mostly upright, about 10° from vertical. Texture and luster: Smooth, glabrous; matte. Color: Close to 63C to 63D.

*Pedicels, sterile flowers*.—Length: About 1.7 cm. Diameter: About 1.5 mm. Strength: Moderately strong. Aspect: About 35° from vertical. Texture and luster: Moderately pubescent; matte. Color: Close to 63C.

*Reproductive organs, fertile flowers*.—Stamens: Quantity per flower: About ten. Filament length: About 3 mm. Filament color: Close to N155D. Anther length: About 1 mm. Anther shape: Oblong. Anther color: Close to 155A. Pollen amount: Moderate. Pollen color: Close to 159D. Pistils: Pistil quantity per flower: About three or four. Pistil length: About 1 mm. Stigma shape: Club-shaped. Stigma color: Close to N155B. Style length: About 0.5 mm. Style color: Close to 69D. Ovary color: Close to 150D.

*Reproductive organs, sterile flowers*.—Stamens: Quantity per flower: About eight. Filament length: About 3 mm. Filament color: Close to N155D. Anther length: About 1 mm. Anther shape: Oblong. Anther color: Close to 155A. Pollen amount: Moderate. Pollen color: Close to 159D. Pistils: Pistil quantity per flower: About three. Pistil length: About 1 mm. Stigma shape: Club-shaped. Stigma color: Close to N155B. Style length: About 0.5 mm. Style color: Close to 69D. Ovary color: Close to 157D.

*Seeds*.—Seed development has not been observed on plants of the new *Hydrangea* to date.

Disease & pest resistance: Under commercial production conditions, plants of the new *Hydrangea* have not been observed to be resistant to pathogens and pests common to *Hydrangea* plants.

Temperature tolerance: Plants of the new *Hydrangea* have been shown to be suitable for USDA Hardiness Zones 5 to 9.

It is claimed:

1. A new and distinct *Hydrangea* plant named 'Hortmablush' as illustrated and described.

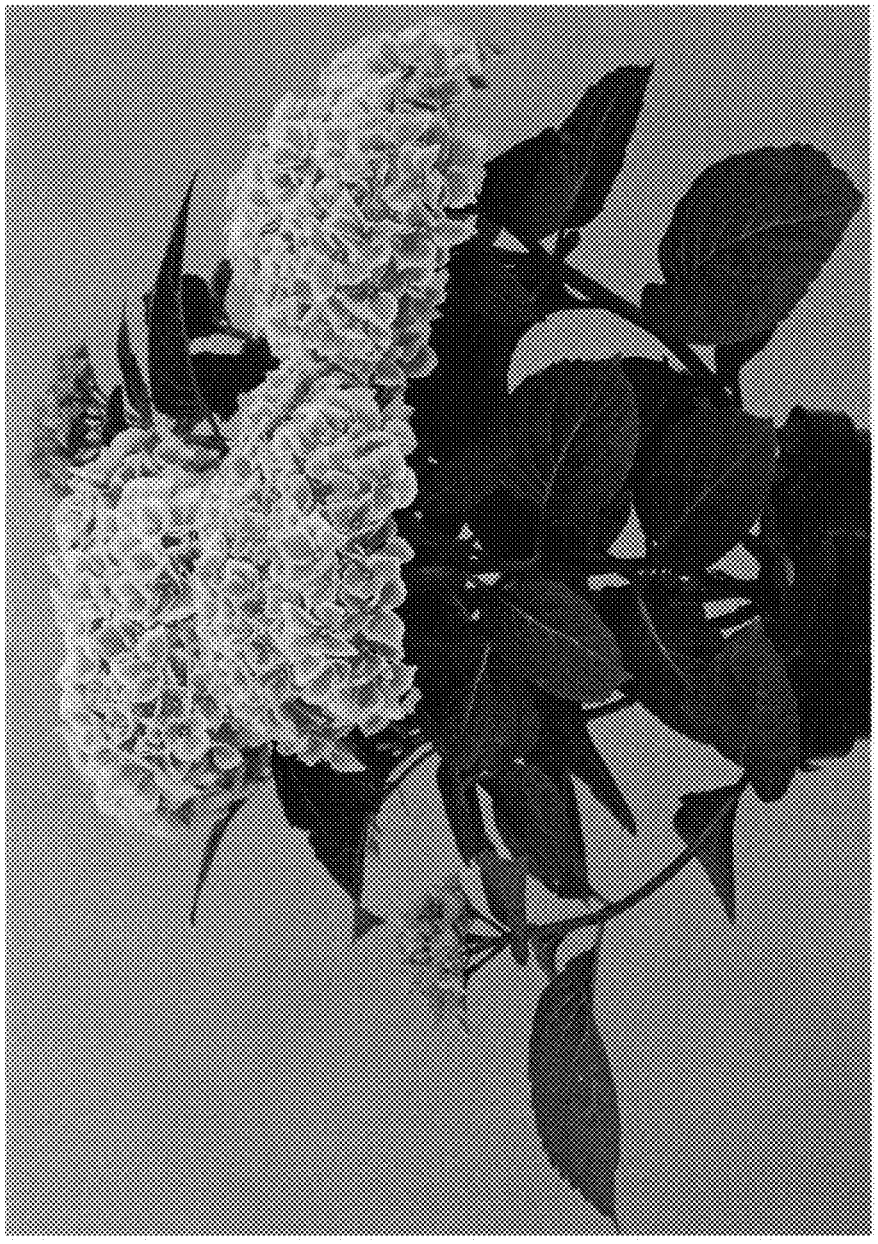

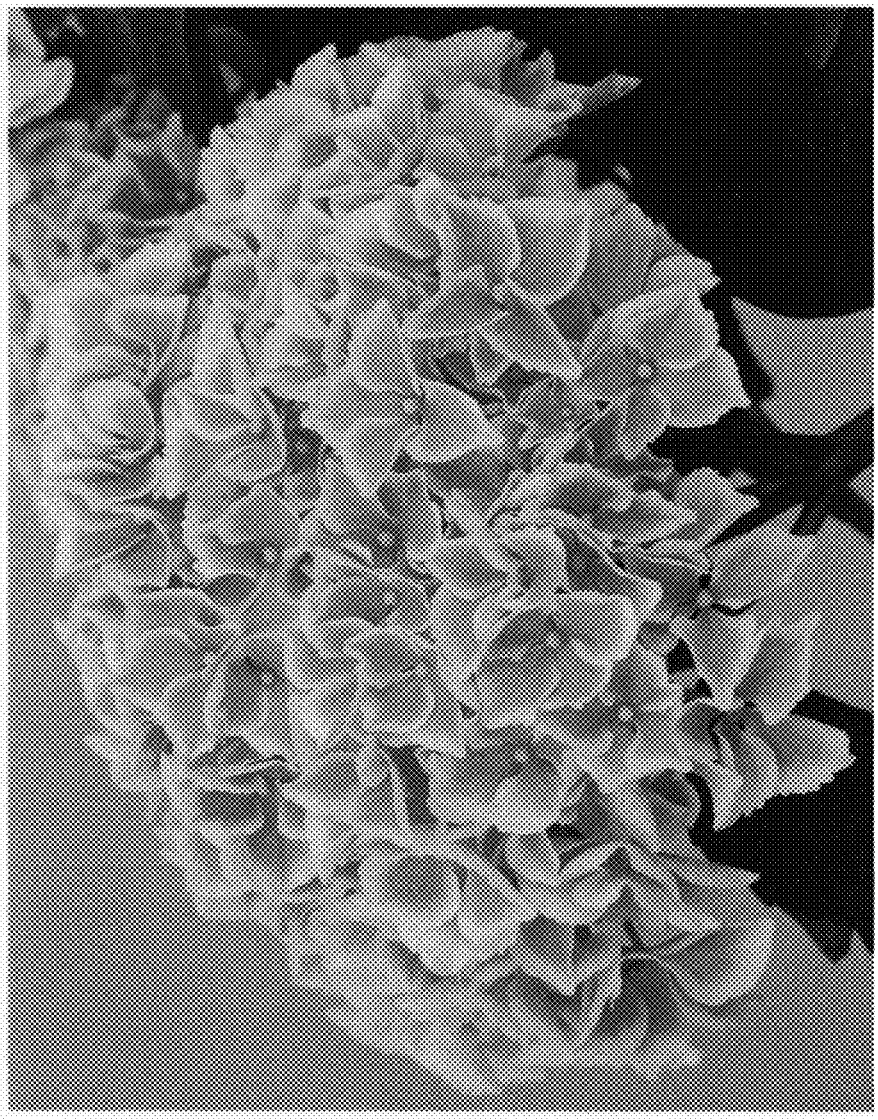

* * * * *